(12) United States Patent
Guggenheim et al.

(10) Patent No.: US 7,115,785 B2
(45) Date of Patent: Oct. 3, 2006

(54) METHOD FOR MAKING SALTS HYDROXY-SUBSTITUTED HYDROCARBONS

(75) Inventors: Thomas Link Guggenheim, Mt. Vernon, IN (US); Daniel Joseph Brunelle, Burnt Hills, NY (US); David Winfield Woodruff, Clifton Park, NY (US); Lee Harris Bergman, Houston, TX (US); Norman Enoch Johnson, Mt. Vernon, IN (US); Matthew Hal Littlejohn, Green Island, NY (US); Farid Fouad Khouri, Clifton Park, NY (US)

(73) Assignee: General Electric Company, Niskayuna, NY (US)

( * ) Notice: Subject to any disclaimer, the term of this patent is extended or adjusted under 35 U.S.C. 154(b) by 588 days.

(21) Appl. No.: 10/647,890

(22) Filed: Aug. 25, 2003

(65) Prior Publication Data
US 2005/0049439 A1 Mar. 3, 2005

(51) Int. Cl.
*C07C 37/68* (2006.01)
*C07C 39/16* (2006.01)

(52) U.S. Cl. ............ 568/723; 568/716; 568/763; 568/753; 568/722; 568/724; 568/852; 568/902

(58) Field of Classification Search ............ 568/723, 568/716, 763, 753, 722, 724, 852, 902
See application file for complete search history.

(56) References Cited

U.S. PATENT DOCUMENTS

| | | | |
|---|---|---|---|
| 1,955,080 A | 4/1934 | Mills |
| 2,991,273 A | 7/1961 | Hechelhammer et al. |
| 2,999,835 A | 9/1961 | Goldberg |
| 3,028,365 A | 4/1962 | Schnell et al. |
| 3,148,172 A | 9/1964 | Fox |
| 3,205,198 A | 9/1965 | Deanin et al. |
| 3,247,164 A | 4/1966 | Caldwell |
| 3,271,367 A | 9/1966 | Schnell et al. |
| 3,271,368 A | 9/1966 | Goldberg et al. |
| 3,847,869 A | 11/1974 | Williams |
| 3,852,242 A | 12/1974 | White |
| 3,879,428 A | 4/1975 | Heath et al. |
| 3,960,968 A | 6/1976 | Vernaleken et al. |
| 3,974,084 A | 8/1976 | Pietzsch et al. |
| 4,093,600 A | 6/1978 | Fan et al. |
| 4,108,837 A | 8/1978 | Johnson et al. |
| 4,175,175 A | 11/1979 | Johnson et al. |
| 4,183,874 A | 1/1980 | Fan et al. |
| 4,202,993 A | 5/1980 | Takekoshi |
| 4,217,438 A | 8/1980 | Brunelle et al. |
| 4,257,953 A | 3/1981 | Williams et al. |
| 4,273,712 A | 6/1981 | Williams |
| 4,302,616 A | 11/1981 | Williams et al. |
| 4,363,892 A | 12/1982 | Shain |
| 4,410,735 A | 10/1983 | Dellacoletta et al. |
| 4,451,330 A | 5/1984 | Vitner |
| 4,492,806 A | 1/1985 | Mendiratta et al. |
| 4,520,204 A | 5/1985 | Evans |
| 4,546,207 A | 10/1985 | Mendiratta et al. |
| 4,740,330 A | 4/1988 | Wang et al. |
| 5,068,353 A | 11/1991 | Dellacoletta |
| 5,096,991 A | 3/1992 | Kozakai |
| 5,157,105 A | 10/1992 | Corley et al. |
| 5,194,570 A | 3/1993 | Kohn et al. |
| 5,229,482 A | 7/1993 | Brunelle |
| 5,242,997 A | 9/1993 | Kohn et al. |
| 5,275,758 A | 1/1994 | Wulff et al. |
| 5,663,275 A | 9/1997 | Schmidhauser |
| 5,830,974 A | 11/1998 | Schmidhauser et al. |
| 5,851,837 A | 12/1998 | Stokes et al. |
| 5,959,160 A | 9/1999 | Wulff et al. |
| 2002/0037838 A1 | 3/2002 | Kono et al. |
| 2002/0045715 A1 | 4/2002 | Takekoshi |
| 2002/0045716 A1 | 4/2002 | Takekoshi |
| 2002/0049286 A1 | 4/2002 | Takekoshi |

FOREIGN PATENT DOCUMENTS

| | | |
|---|---|---|
| DE | 2456446 | 8/1976 |
| DE | 4129545 | 4/1993 |
| EP | 0117459 | 9/1984 |
| FR | 2206760 | 6/1974 |
| GB | 1133561 | 11/1968 |
| GB | 1414424 | 11/1975 |
| GB | 1454852 | 11/1976 |
| JP | 63027448 | 2/1988 |
| JP | 63159332 | 7/1988 |

*Primary Examiner*—Elvis O. Price
(74) *Attorney, Agent, or Firm*—Andrew J. Caruso; William E. Powell, III

(57) ABSTRACT

Disclosed is a method for preparing an alkali metal salt of a hydroxy-substituted hydrocarbon which comprises the steps of (i) contacting in solvent media at least one hydroxy-substituted hydrocarbon with a base comprising an alkali metal cation; and (ii) devolatilizing the solvent media comprising alkali metal salt by adding or spraying the solvent media into a substantially water-immiscible organic solvent, said solvent being at a temperature greater than the boiling point of solvent media at the prevailing pressure. In one embodiment the solvent media comprises water, and optionally at least one water-soluble protic organic solvent.

70 Claims, No Drawings

US 7,115,785 B2

METHOD FOR MAKING SALTS HYDROXY-SUBSTITUTED HYDROCARBONS

BACKGROUND OF INVENTION

This invention relates to methods for making salts of hydroxy-substituted alkyl or aromatic hydrocarbons. In one particular embodiment the invention relates to the preparation of alkali metal salts of hydroxy-substituted alkyl or aromatic hydrocarbons.

Salts of hydroxy-substituted hydrocarbons are frequently required for synthesis of hydroxy-substituted hydrocarbon derivatives or for use as bases in chemical reactions to name just two of their many uses. For example, salts of hydroxy-substituted aromatic hydrocarbons (sometimes referred to as phenate salts) are frequently required for synthesis of hydroxy-substituted aromatic hydrocarbon derivatives. In some embodiments salts of dihydroxy-substituted aromatic hydrocarbons are used in the preparation of monomers for use in condensation polymerization to form polymers with structural units derived from said dihydroxy-substituted aromatic hydrocarbons. For example, alkali metal salts of dihydroxy-substituted aromatic hydrocarbons may be employed in displacement reactions with appropriately substituted phthalimides to prepare monomers for use in synthesis of polyetherimides. Salts of dihydroxy-substituted aromatic hydrocarbons may also be used themselves as monomers in condensation polymerization. For example, alkali metal salts of dihydroxy-substituted aromatic hydrocarbons may participate in polymerization reactions with appropriately substituted aromatic bis(substituted phthalimide)s to prepare polyetherimides directly. In particular examples U.S. Pat. No. 5,229,482 discloses a displacement method for the preparation of polyetherimides from bis(chlorophthalimides) and alkali metal salts of dihydroxy-substituted aromatic hydrocarbons using a solvent of low polarity such as o-dichlorobenzene in the presence of a thermally stable phase transfer catalyst such as a hexaalkylguanidinium halide. U.S. Pat. No. 5,830,974 discloses a similar method using a monoalkoxybenzene such as anisole as solvent. These methods made it possible for the first time to envision the commercial production of polyetherimides and other condensation polymers by a displacement method. Nevertheless, several problems remain to be solved for the optimum development of the displacement reaction for condensation polymer preparation. In particular a reliable method is needed for synthesis of alkali metal salts of hydroxy-substituted hydrocarbons and particularly hydroxy-substituted aromatic hydrocarbons on a large scale.

U.S. Pat. No. 4,520,204 describes the manufacture of salts such as bisphenol A disodium salt by forming the salt in an aqueous solution with sodium hydroxide and adding the aqueous solution to refluxing ortho-dichlorobenzene with removal of water to afford a salt slurry. The salt slurry in organic solvent is further dried by refluxing over calcium hydride or by azeotropic removal of water with an organic solvent. The procedure is problematic in that foaming may occur during the addition of the aqueous salt solution to the refluxing ortho-dichlorobenzene.

U.S. Pat. No. 4,546,207 describes the manufacture of anhydrous salts of dihydroxyaromatic compounds by forming the salt in an aqueous solution with excess sodium hydroxide and then isolating the solid salt from the reaction mixture. The solid salt is then treated with an organic solvent and the mixture evaporated to dry the salt. In this procedure the salt may be obtained as a hydrate with varying degree of hydration making it difficult to do stoichiometry calculation in subsequent reactions.

BRIEF SUMMARY OF THE INVENTION

The present invention is based on a series of studies that have identified solutions for the problems associated with the preparation of alkali metal salts of hydroxy-substituted hydrocarbons using previous methods.

In a particular embodiment the present invention is a method for preparing an alkali metal salt of a hydroxy-substituted hydrocarbon which comprises the steps of (i) contacting in a solvent media at least one hydroxy-substituted hydrocarbon with a base comprising an alkali metal cation; and (ii) devolatilizing the solvent media comprising alkali metal salt by spraying the solvent media into a substantially water-immiscible organic solvent, said organic solvent being at a temperature greater than the boiling point of said solvent media at the prevailing pressure.

Various other features, aspects, and advantages of the present invention will become more apparent with reference to the following description and appended claims.

DETAILED DESCRIPTION OF THE INVENTION

In this specification and in the claims that follow, reference will be made to a number of terms that shall be defined to have the following meaning. The singular forms "a", "an" and "the" include plural referents unless the context clearly dictates otherwise. The terms "optional" or "optionally" mean that the subsequently described event or circumstance may or may not occur, and that the description includes instances where said event or circumstance occurs and instances where it does not.

The term "alkyl" as used in the various embodiments of the present invention is intended to designate moieties which may be normal alkyl, branched alkyl, aralkyl, cycloalkyl, bicycloalkyl and tricycloalkyl radicals containing from 1 to about 30 carbon atoms. In various embodiments normal and branched alkyl radicals include as illustrative non-limiting examples methyl, ethyl, n-propyl, isopropyl, n-butyl, sec-butyl, tertiary-butyl, pentyl, neopentyl, hexyl, heptyl, octyl, nonyl, decyl, undecyl and dodecyl. In some embodiments cycloalkyl radicals are those containing from 3 to about 12 ring carbon atoms. Some illustrative non-limiting examples of cycloalkyl radicals include cyclobutyl, cyclopentyl, cyclohexyl, methylcyclohexyl, and cycloheptyl. Some illustrative non-limiting examples of bicycloalkyl and tricycloalkyl radicals include bicyclo[2.2.1]heptyl and adamantyl. In some embodiments aralkyl radicals are those containing from 7 to about 14 carbon atoms; these include, but are not limited to, benzyl, phenylbutyl, phenylpropyl, and phenylethyl. Aryl radicals used in the various embodiments of the present invention comprise those containing from 6 to 18 ring carbon atoms. Some illustrative non-limiting examples of these aryl radicals include phenyl, toluyl, xylyl, biphenyl, and naphthyl.

Suitable hydroxy-substituted hydrocarbons for use in the present invention include both hydroxy-substituted alkyl hydrocarbons and hydroxy-substituted aromatic hydrocarbons. Hydroxy-substituted alkyl hydrocarbons for use in the present invention may optionally bear at least one other substituent and include monohydroxy-substituted alkyl hydrocarbons. Illustrative examples of monohydroxy-substituted alkyl hydrocarbons include, but are not limited to, methanol, ethanol, n-propanol, isopropanol, 1-butanol, 2-butanol, cyclohexanol, 2-norbornanemethanol, abenzyl alcohol, and the like. Suitable hydroxy-substituted alkyl hydrocarbons also include dihydroxy-substituted alkyl hydrocarbons and alkyl hydrocarbons with multiple hydroxy groups, such as, but not limited to, trihydroxy-substituted alkyl hydrocarbons and tetrahydroxy-substituted alkyl hydrocarbons. Illustrative examples of suitable dihydroxy-substituted alkyl hydrocarbons comprise alpha,omega-alkyl diols, ethylene glycol, 1,2-propanediol, 1,3-propanediol, 1,4-butanediol, cyclohexanedimethanol, 1,4-cyclohexanedimethanol, benzenedimethanol, 1,4-benzenedimethanol, and the like. Suitable hydroxy-substituted alkyl hydrocarbons also include thiohydroxy-substituted alkyl hydrocarbons and in particular thiohydroxy-substituted alkyl hydrocarbons corresponding to any hydroxy-substituted alkyl hydrocarbon described herein obtained by replacing one or more hydroxy groups with thiohydroxy groups.

Suitable hydroxy-substituted aromatic hydrocarbons for use in the present invention may optionally bear at least one other substituent and include monohydroxy-substituted aromatic hydrocarbons. Illustrative examples of monohydroxy-substituted aromatic hydrocarbons include, but are not limited to, phenol, alkyl phenols, o-cresol, m-cresol, p-cresol, p-cumylphenol, resorcinol monomethyl ether, 1-naphthol, 2-naphthol, p-chlorophenol, o-chlorophenol and other monohydroxy-substituted aromatic hydrocarbons described herein. Suitable hydroxy-substituted aromatic hydrocarbons also include dihydroxy-substituted aromatic hydrocarbons and aromatic hydrocarbons with multiple hydroxy groups, such as, but not limited to, trihydroxy-substituted aromatic hydrocarbons and tetrahydroxy-substituted aromatic hydrocarbons. Suitable hydroxy-substituted aromatic hydrocarbons also include thiohydroxy-substituted aromatic hydrocarbons and in particular thiohydroxy-substituted aromatic hydrocarbons corresponding to any hydroxy-substituted aromatic hydrocarbon described herein obtained by replacing one or more hydroxy groups with thiohydroxy groups.

In some particular embodiments suitable hydroxy-substituted aromatic hydrocarbons comprise dihydroxy-substituted aromatic hydrocarbons represented by the formula (I):

HO---D---OH (I)

wherein D is a divalent aromatic radical. In some embodiments, D has the structure of formula (II):

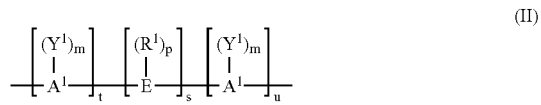

(II)

wherein $A^1$ represents an aromatic group including, but not limited to, phenylene, biphenylene, naphthylene, etc. In some embodiments E may be an alkylene or alkylidene group including, but not limited to, methylene, ethylene, ethylidene, propylene, propylidene, isopropylidene, butylene, butylidene, isobutylidene, amylene, amylidene, isoamylidene, etc. In other embodiments when E is an alkylene or alkylidene group, it may also consist of two or more alkylene or alkylidene groups connected by a moiety different from alkylene or alkylidene, including, but not limited to, an aromatic linkage; a tertiary nitrogen linkage; an ether linkage; a carbonyl linkage; a silicon-containing linkage, including, but not limited to, a silane; or a sulfur-containing linkage including, but not limited to, sulfide, sulfoxide, sulfone, etc.; or a phosphorus-containing linkage including, but not limited to, phosphinyl, phosphonyl, etc. In other embodiments E may be a cycloaliphatic group including, but not limited to, cyclopentylidene, 3,3,5-trimethylcyclopentylidene, cyclohexylidene, 3,3-dimethylcyclohexylidene, 3,3,5-trimethylcyclohexylidene, methylcyclohexylidene, 2-[2.2.1]-bicycloheptylidene, neopentylidene, cyclopentadecylidene, cyclododecylidene, adamantylidene, etc.; a sulfur-containing linkage, including, but not limited to, sulfide, sulfoxide or sulfone; a phosphorus-containing linkage, including, but not limited to, phosphinyl or phosphonyl; an ether linkage; a carbonyl group; a tertiary nitrogen group; or a silicon-containing linkage including, but not limited to, a silane. $R^1$ represents hydrogen or a monovalent hydrocarbon group including, but not limited to, alkenyl, allyl, alkyl, aryl, aralkyl, alkaryl, or cycloalkyl. In various embodiments a monovalent hydrocarbon group of $R^1$ may be halogen-substituted, particularly fluoro- or chloro-substituted, for example as in dichloroalkylidene, particularly gem-dichloroalkylidene. $Y^1$ independently at each occurrence is selected from the group consisting of an inorganic atom including, but not limited to, halogen (fluorine, bromine, chlorine, iodine); an inorganic group containing more than one inorganic atom including, but not limited to, nitro; an organic group including, but not limited to, a monovalent hydrocarbon group including, but not limited to, alkenyl, allyl, alkyl, aryl, aralkyl, alkaryl, or cycloalkyl, or an oxy group including, but not limited to, $OR^2$ wherein $R^2$ is a monovalent hydrocarbon group including, but not limited to, alkyl, aryl, aralkyl, alkaryl, or cycloalkyl, it being only necessary that $Y^1$ be inert to and unaffected by the reactants and reaction conditions used to prepare the polymer. In some particular embodiments $Y^1$ comprises a halo group or $C_1$–$C_6$ alkyl group. The letter "m" represents any integer from and including zero through the number of positions on $A^1$ available for substitution; "p" represents an integer from and including zero through the number of positions on E available for substitution; "t" represents an integer equal to at least one; "s" represents an integer equal to either zero or one; and "u" represents any integer including zero.

In dihydroxy-substituted aromatic hydrocarbons in which D is represented by formula (II) above, when more than one $Y^1$ substituent is present, they may be the same or different. The same holds true for the $R^1$ substituent. Where "s" is zero in formula (II) and "u" is not zero, the aromatic rings are directly joined by a covalent bond with no intervening alkylidene or other bridge. The positions of the hydroxyl groups and $Y^1$ on the aromatic nuclear residues $A^1$ can be varied in the ortho, meta, or para positions and the groupings can be in vicinal, asymmetrical or symmetrical relationship, where two or more ring carbon atoms of the hydrocarbon residue are substituted with $Y^1$ and hydroxyl groups. In some particular embodiments the parameters "t", "s", and "u" each have the value of one; both $A^1$ radicals are unsubstituted phenylene radicals; and E is an alkylidene group such as isopropylidene. In some particular embodiments both $A^1$ radicals are p-phenylene, although both may be o- or m-phenylene or one o- or m-phenylene and the other p-phenylene.

In some embodiments of dihydroxy-substituted aromatic hydrocarbons E in formula (II) may be an unsaturated alkylidene group. Suitable dihydroxy-substituted aromatic hydrocarbons of this type include, but are not limited to, those of the formula (III):

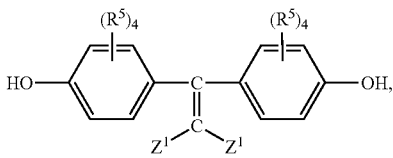

where independently each $R^5$ is hydrogen, chlorine, bromine or a $C_{1-30}$ monovalent hydrocarbon or hydrocarbonoxy group, each $Z^1$ is hydrogen, chlorine or bromine, subject to the provision that at least one $Z^1$ is chlorine or bromine.

Suitable dihydroxy-substituted aromatic hydrocarbons also include those of the formula (IV):

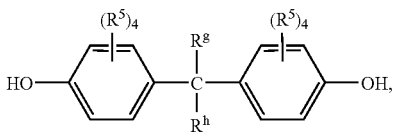

where independently each $R^5$ is as defined hereinbefore, and independently $R^g$ and $R^h$ are hydrogen or a $C_{1-30}$ hydrocarbon group.

In some embodiments of the present invention dihydroxy-substituted aromatic hydrocarbons that may be used include those disclosed by name or formula (generic or specific) in U.S. Pat. Nos. 2,991,273, 2,999,835, 3,028,365, 3,148,172, 3,271,367, 3,271,368, and 4,217,438. In other embodiments of the invention hydroxy-substituted aromatic hydrocarbons include 4,4'-(cyclopentylidene)diphenol; 4,4'-(3,3,5-trimethylcyclopentylidene)diphenol; 4,4'-(cyclohexylidene)diphenol; 4,4'-(3,3-dimethylcyclohexylidene)diphenol; 4,4'-(3,3,5-trimethylcyclohexylidene)diphenol; 4,4'-(methylcyclohexylidene)diphenol; 4,4'-bis(3,5-dimethyl)diphenol; 1,1-bis(4-hydroxy-3-methylphenyl)cyclohexane; 4,4-bis(4-hydroxyphenyl)heptane; 2,4'-dihydroxydiphenylmethane; bis(2-hydroxyphenyl)methane; bis(4-hydroxyphenyl)methane; bis(4-hydroxy-5-nitrophenyl)methane; bis(4-hydroxy-2,6-dimethyl-3-methoxyphenyl)methane; 1,1-bis(4-hydroxyphenyl)ethane; 1,2-bis(4-hydroxyphenyl)ethane; 1,1-bis(4-hydroxy-2-chlorophenyl)ethane; 2,2-bis(4-hydroxyphenyl)propane (commonly known as bisphenol A); 2,2-bis(3-phenyl-4-hydroxyphenyl)propane; 2,2-bis(4-hydroxy-3-methylphenyl)propane; 2,2-bis(4-hydroxy-3-ethylphenyl)propane; 2,2-bis(4-hydroxy-3-isopropylphenyl)propane; 2,2-bis(4-hydroxy-3,5-dimethylphenyl)propane; 3,5,3',5'-tetrachloro-4,4'-dihydroxyphenyl)propane; bis(4-hydroxyphenyl)cyclohexylmethane; 2,2-bis(4-hydroxyphenyl)-1-phenylpropane; 2,4'-dihydroxyphenyl sulfone; dihydroxy naphthalene, 2,6-dihydroxy naphthalene; catechol; hydroquinone; resorcinol; $C_{1-3}$ alkyl-substituted resorcinols; 2,2-bis(4-hydroxyphenyl)butane; 2,2-bis(4-hydroxyphenyl)-2-methylbutane; 1,1-bis(4-hydroxyphenyl)cyclohexane; biphenol; bis(4-hydroxyphenyl); bis(4-hydroxyphenyl) ether; bis(4-hydroxyphenyl)sulfide; 2-(3-methyl-4-hydroxyphenyl-2-(4-hydroxyphenyl)propane; 2-(3,5-dimethyl-4-hydroxyphenyl)-2-(4-hydroxyphenyl)propane; 2-(3-methyl-4-hydroxyphenyl)-2-(3,5-dimethyl-4-hydroxyphenyl)propane; bis(3,5-dimethylphenyl-4-hydroxyphenyl)methane; 1,1-bis(3,5-dimethylphenyl-4-hydroxyphenyl)ethane; 2,2-bis(3,5-dimethylphenyl-4-hydroxyphenyl)propane; 2,4-bis(3,5-dimethylphenyl-4-hydroxyphenyl)-2-methylbutane; 3,3-bis(3,5-dimethylphenyl-4-hydroxyphenyl)pentane; 1,1-bis(3,5-dimethylphenyl-4-hydroxyphenyl)cyclopentane; 1,1-bis(3,5-dimethylphenyl-4-hydroxyphenyl)cyclohexane; bis(3,5-dimethylphenyl-4-hydroxyphenyl)sulfide; and tris(4-hydroxyphenyl)ethane. In a particular embodiment the dihydroxy-substituted aromatic hydrocarbon comprises bisphenol A.

In some embodiments of dihydroxy-substituted aromatic hydrocarbons when E in formula (II) is an alkylene or alkylidene group, said group may be part of one or more fused rings attached to one or more aromatic groups bearing one hydroxy substituent. Suitable dihydroxy-substituted aromatic hydrocarbons of this type include those containing indane structural units such as represented by the formula (V), which compound is 3-(4-hydroxyphenyl)-1,1,3-trimethylindan-5-ol, and by the formula (VI), which compound is 1-(4-hydroxyphenyl)-1,3,3-trimethylindan-5-ol:

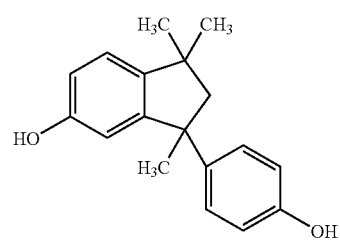

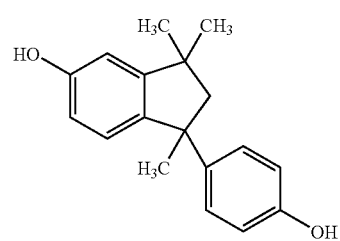

Also included among suitable dihydroxy-substituted aromatic hydrocarbons of the type comprising one or more alkylene or alkylidene groups as part of fused rings are the 2,2,2',2'-tetrahydro-1,1'-spirobi[1H-indene]diols having formula (VII)

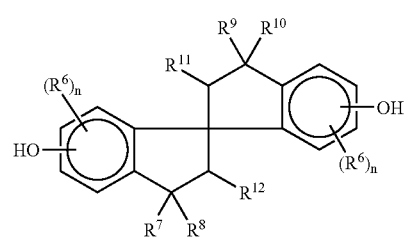

wherein each $R^6$ is independently selected from monovalent hydrocarbon radicals and halogen radicals; each $R^7$, $R^8$, $R^9$, and $R^{10}$ is independently $C_{1-6}$ alkyl; each $R^{11}$ and $R^{12}$ is independently H or $C_{1-6}$ alkyl; and each n is independently selected from positive integers having a value of from 0 to 3 inclusive. In a particular embodiment the 2,2,2',2'-tetrahydro-1,1'-spirobi[1H-indene]diol is 2,2,2',2'-tetrahydro-3,3,3',3'-tetramethyl-1,1'-spirobi[1H-indene]-6,6'-diol (sometimes known as "SBI").

Mixtures comprising two or more hydroxy-substituted hydrocarbons may also be employed. In some particular embodiments mixtures of at least two monohydroxy-substituted alkyl hydrocarbons, or mixtures of at least one monohydroxy-substituted alkyl hydrocarbon and at least one dihydroxy-substituted alkyl hydrocarbon, or mixtures of at least two dihydroxy-substituted alkyl hydrocarbons, or mixtures of at least two monohydroxy-substituted aromatic hydrocarbons, or mixtures of at least two dihydroxy-substituted aromatic hydrocarbons, or mixtures of at least one monohydroxy-substituted aromatic hydrocarbon and at least one dihydroxy-substituted aromatic hydrocarbon, or mixtures of at least one monohydroxy-substituted alkyl hydrocarbon and at least one dihydroxy-substituted aromatic hydrocarbon may be employed.

The salts of hydroxy-substituted hydrocarbons which may be prepared by the method of the present invention are in one embodiment alkali metal salts comprising cations of either lithium, sodium, potassium, rubidium or cesium. In particular embodiments alkali metal salts of hydroxy-substituted hydrocarbons are sodium or potassium salts. Sodium salts are often used in some particular embodiments by reason of their availability and relatively low cost.

In some embodiments of the invention the salt of a hydroxy-substituted hydrocarbon may be prepared by a method which includes a step of contacting in solvent media at least one hydroxy-substituted hydrocarbon and at least one base. Solvent media in the present context refers to media comprising at least one solvent in which a hydroxy-substituted hydrocarbon reacts to form salt in the presence of base. In particular embodiments said solvent media comprises at least one solvent in which a hydroxy-substituted hydrocarbon is at least partially soluble or said solvent media comprises at least one solvent in which the salt of a hydroxy-substituted hydrocarbon is at least partially soluble. In another particular embodiment said solvent media is such that a hydroxy-substituted hydrocarbon is essentially completely soluble therein. In another particular embodiment said solvent media is such that the salt of a hydroxy-substituted hydrocarbon is essentially completely soluble therein, in which case a clear solution of salt in solvent media may be obtained. In another particular embodiment said hydroxy-substituted hydrocarbon is solubilized in the presence of base with formation of salt. In another particular embodiment said solvent media is a hydroxy-substituted hydrocarbon. In another particular embodiment said solvent media comprises water and, optionally, at least one substantially water-soluble protic organic solvent. In yet another particular embodiment said solvent media comprises at least one substantially water-soluble protic organic solvent and, optionally, water. Substantially water-soluble in the present context refers to a solubility of the protic organic solvent in water of greater than about 90% or greater than about 95% or greater than about 98% or greater than about 99% by weight under the reactions conditions, or to a solubility of water in protic organic solvent of greater than about 90% or greater than about 95% or greater than about 98% or greater than about 99% by weight under the reactions conditions. Water-soluble protic organic solvents are well-known in the art and comprise alkyl alcohols such as, but not limited to, methanol, ethanol, propanol, butanol, ethylene glycol, propylene glycol, and the like. Mixtures of protic organic solvents may also be employed. When solvent media comprises water and at least one substantially water-soluble protic organic solvent, then the amount of said protic organic solvent may be in a range of between about 1% and about 99%, or in a range of between about 10% and about 90%, in a range of between about 20% and about 80%, or in a range of between about 30% and about 70%, or in a range of between about 40% and about 60%, by weight based on the total weight of protic organic solvent and water. In some particular embodiments the amount of said protic organic solvent, when present, may be sufficient to effect essentially complete solubility of hydroxy-substituted hydrocarbon in a mixture with water.

When solvent media comprises water and at least one substantially water-soluble protic organic solvent, then the solvent media comprising salt may be added to an organic solvent for devolatilization by any convenient means, including, but not limited to, spraying, pumping through a pipe, adding dropwise, adding in batches, semicontinuously or continuously. In some particular embodiments it has been found that the use of solvent media comprising water and at least one substantially water-soluble protic organic solvent may result in little or no foaming during addition of solvent media comprising salt to organic solvent and also may result in salt with less tendency to cake than when at least one substantially water-soluble protic organic solvent is absent.

The order of combining hydroxy-substituted hydrocarbon, solvent media and base may be accomplished by any convenient method. In various illustrative, non-limiting embodiments the hydroxy-substituted hydrocarbon may be combined with water and treated with aqueous base, or the hydroxy-substituted hydrocarbon may be combined with at least one water-soluble protic organic solvent and treated with aqueous base, or the hydroxy-substituted hydrocarbon may be combined with at least one water-soluble protic organic solvent and treated with non-aqueous base, or the hydroxy-substituted hydrocarbon may be combined with water and at least one water-soluble protic organic solvent and treated with aqueous base, or the hydroxy-substituted hydrocarbon may be treated with solid base.

In one particular embodiment an alkali metal salt of a dihydroxy-substituted aromatic hydrocarbon may be prepared by contacting at least one dihydroxy-substituted aromatic hydrocarbon and at least one alkali metal hydroxide in a solvent media comprising water and, optionally, methanol. In a particular embodiment the alkali metal hydroxide is sodium hydroxide. The base may be employed in any convenient form. In some embodiments the base is employed as an aqueous solution. In an illustrative example an aqueous solution containing about 30–70% by weight of an alkali metal hydroxide is suitable. Solutions comprising about 50% by weight concentration of alkali metal hydroxide are readily available and their use may be preferred. In other embodiments the base is employed as a solution comprising at least one water-soluble protic organic solvent, illustrative examples of which comprise those described herein above. When the base is employed as a solution comprising at least one water-soluble protic organic solvent, then illustrative examples of suitable bases comprise alkali metal salts of at least one water-soluble protic organic solvent. In other particular embodiments a solid base is used. Illustrative, non-limiting examples of solid bases comprise alkali metal elements such as, but not limited to, sodium metal; alkali metal hydrides such as, but not limited to, sodium hydride; alkali metal alkoxides such as, but not limited to, sodium alkoxides and sodium methoxide; and alkali metal hydroxides such as, but not limited to, sodium hydroxide and potassium hydroxide.

Contact may be performed using amounts of hydroxy-substituted hydrocarbon and base which in various embodiments are stoichiometric, or deviate from stoichiometry by an amount in a range of between about 0.01 and about 1.2 mole %, or by an amount in a range of between about 0.05 and about 1.2 mole %. A deviation from stoichiometry of 0.01 mole % or less is considered to be essentially stoichiometric. In some particular embodiments the amounts of hydroxy-substituted hydrocarbon and base deviate from stoichiometry by no more than plus/minus 1 mole %, or by no more than plus/minus 0.9 mole %, or by no more than plus/minus 0.8 mole %, or by no more than plus/minus 0.7 mole %, or by no more than plus/minus 0.6 mole %. In other particular embodiments the amounts of hydroxy-substituted hydrocarbon and base deviate from stoichiometry by no more than plus/minus 0.1 mole %, or by no more than plus/minus 0.2 mole %, or by no more than plus/minus 0.3 mole %, or by no more than plus/minus 0.4 mole %. Said contact may be performed in solvent media at a temperature in various embodiments of above about 20° C., or of above about 30° C., or of above about 40° C., or of above about 50° C., or of above about 60° C., or of above about 70° C., or of above about 80° C., or of above about 90° C. In a particular embodiment said contact is performed at a temperature in a range of between about 90° C. and about 100° C. In some particular embodiments a hydroxy-substituted hydrocarbon may be contacted with base at one temperature whereupon the mixture may exotherm to a higher temperature and may optionally be heated to still a higher temperature until the desired degree of conversion to salt is obtained. In other particular embodiments a hydroxy-substituted hydrocarbon may be diluted with water or with water-soluble protic organic solvent or with both water and water-soluble protic organic solvent before contact with base. Said contact may typically be effected for a period of time sufficient to form the desired degree of conversation to alkali metal salt. The said contact time depends upon a number of factors including, but not limited to, the amounts of hydroxy-substituted hydrocarbon and base reactants. Often, contact for a sufficient time to mix the reactants or for greater than about 10 minutes or for greater than about 0.5 hours or for greater than about 1 hour or for about 1.5–3 hours is sufficient. In a particular embodiment contact is for a time sufficient to form a clear solution of salt in solvent media. Appropriate contact times depend upon reaction temperatures and the nature of the reactants among other factors and may be determined by one skilled in the art without undue experimentation. Said contact may be performed under an inert atmosphere, such as under nitrogen. Said contact may be performed at a solids level of in various embodiments greater than about 5%, or greater than about 10%, or greater than about 15%, or greater than about 20%, or greater than about 25%, wherein solids level is weight reactants divided by the sum of weight reactants and weight solvent. In some particular embodiments said contact is performed at a solids level in a range of between about 26% and about 31%, or at a solids level in a range of between about 27% and about 30%. The course of the reaction may be monitored by known methods.

The salt reaction product in solvent media may be substantially devolatilized and prepared typically as a slurry at least partially insoluble in an organic solvent by contacting the solvent media comprising the salt reaction product with a substantially water-immiscible organic solvent having a boiling point above that of solvent media, and substantially removing the solvent media. In some embodiments the salt reaction product is at least partially insoluble in the organic solvent at the temperature of devolatilizing. In other embodiments the salt reaction product is substantially insoluble in the organic solvent at the temperature of devolatilizing, meaning that said salt reaction product is less than about 10 wt. % soluble, or less than about 5 wt. % soluble, or less than about 2 wt. % soluble, or less than about 1 wt. % soluble in said organic solvent. Substantially devolatilized in the present context means that greater than about 90 wt. %; or greater than about 95 wt. %; or greater than about 98 wt. %; or greater than about 99 wt. %; or greater than about 99.4 wt. %; or greater than about 99.6 wt. %; or greater than about 99.9 wt. % of the solvent media in the solvent media comprising salt is removed, based on the weight of solvent media originally present in the solvent media comprising salt. Substantially water-immiscible means that the organic solvent dissolves to the extent of less than about 10% by weight or less than about 5% by weight or less than about 1% by weight in water; or that water dissolves to the extent of less than about 10% by weight or less than about 5% by weight or less than about 1% by weight in the organic solvent.

Suitable water-immiscible organic solvents in the present context are those which have a boiling point at atmospheric pressure of greater than about 75° C., or greater than about 100° C., or greater than about 110° C., or greater than about 125° C. In some embodiments suitable solvents also have a density which is in a ratio of about 0.75–1.5 to the density of water at 20–25° C. (wherein the density of water is 0.997 grams per cubic centimeter). In some particular embodiments suitable organic solvents have a density which is in a ratio of greater than 1.1:1, or greater than 1.15:1, or greater than 1.2:1 compared to the density of water at 20–25° C. In some embodiments solvents are aromatic hydrocarbons, and particularly halogenated aromatic hydrocarbons. In particular embodiments solvents comprise cyclohexane, benzene, alkylated benzenes, toluene, xylene, phenetole, anisole, veratrole, diphenylsulfone, halogenated benzenes, chlorinated benzenes such as chlorobenzene, chlorotoluene, dichlorotoluene, 1,2,4-trichlorobenzene, dichlorobenzene, para-dichlorobenzene, and ortho-dichlorobenzene (hereinafter often referred to as ODCB). Mixtures of solvents may also be employed. In some embodiments suitable organic solvents are those which form an azeotrope with solvent media or with water. In one particular embodiment the organic solvent is ortho-dichlorobenzene. In another particular embodiment the organic solvent is toluene.

Said contact of the solvent media comprising salt with a substantially water-immiscible organic solvent may be performed under an inert atmosphere, such as under nitrogen. In one particular embodiment the salt reaction product may be substantially devolatilized by adding the solvent media comprising the salt reaction product to an organic solvent at a temperature above the boiling point of solvent media in such a manner that solvent media is removed from the mixture during the addition and a slurry of salt product in organic solvent results. In another particular embodiment the salt reaction product may be substantially devolatilized by spraying of the solvent media comprising the salt reaction product into an organic solvent at a temperature above the boiling point of solvent media under the prevailing pressure. In some embodiments said solvent media is sprayed at a solids level concentration similar to the solids level at which the salt was prepared. In other embodiments said solvent media may be diluted before spraying. It has been unexpectedly found that spraying of the solvent media (sometimes referred to as atomization of the solvent media) into an organic solvent tends to prevent agglomeration of salt during removal of solvent and also helps prevent foaming of the mixture. In one embodiment the said organic solvent is contained in a vessel (sometimes referred to hereinafter as a dryer). In various embodiments said vessel is agitated for at least a portion of the time of any salt devolatilizing step or during the entire time of any salt devolatilizing step. In one particular embodiment said vessel comprises a stirred tank with at least one stirring shaft agitator. The degree of agitation is typically such as not to favor formation of salt cake in or on any part of the vessel or agitator which may be difficult to remove. In various embodiments the vessel comprises baffles beneath the surface of said organic solvent. At least two baffles may be present. In some embodiments greater than two baffles are present and in other embodiments between two and four baffles may be present. The design of the baffles is such that build-up of salt is not facilitated. In one particular embodiment the baffles are substantially vertical and are attached to the sides of the vessel, optionally starting at the tangent line from a curved surface at the bottom of the vessel should said vessel possess a curved bottom. Any baffle is attached to the side of the vessel at only 1, 2, or 3 or more spots on the baffle so that there is at least a partial gap between any baffle and the side of the vessel such that salt may pass through said gap and not collect to a significant extent against any baffle.

Said vessel containing organic solvent may be fitted with equipment comprising at least one pipe and at least one spray nozzle for introduction of solvent media comprising salt into said vessel. In one embodiment at least one pipe fitted with at least one spray nozzle conveys solvent media comprising salt from the vessel in which the salt was prepared into the vessel containing organic solvent. One, two, three, four or more spray nozzles may be employed for introduction of solvent media comprising salt into said vessel. In some embodiments 1–10 or 2–4 spray nozzles for introduction of solvent media comprising salt are employed. In one embodiment said spray nozzle or nozzles may project into the vessel from the vessel's top. In another embodiment said spray nozzle or nozzles may be mounted flush with the top of the vessel to help prevent caking of salt. The spray of solvent media comprising salt is directed to the top of the organic solvent within the vessel, and preferably away from any agitator shaft and the sides of the vessel. The distance between any spray nozzle and the top of organic solvent level may be any convenient distance to provide for spraying of solvent media comprising salt into the vessel and devolatilization of solvent media with efficient use of the vessel space. In some embodiments a spray nozzle is at a distance of between about 0.15 and 3.0 meters or between about 0.3 and 2.5 meters or between about 0.3 and 1.5 meters or between about 0.3 and 1 meter above the top of the organic solvent level. Any dead space cavities in the vessel may be heated externally or flushed with dry solvent to prevent any accumulation of water or salt cake therein. In one embodiment the vessel sides and top are traced with heating element to provide external heating. In other embodiments provision may be made for contacting the top of the vessel and any dead spaces with hot organic solvent by spraying organic solvent therein. The organic solvent may comprise fresh solvent or solvent returned from condensate which was originally distilled from the vessel along with solvent media, or both fresh and returned solvent. Said spraying of organic solvent may be performed with equipment comprising at least one pipe and at least one spray nozzle for introduction of organic solvent. One, two, three, four or more spray nozzles may be employed for introduction of organic solvent into said vessel. In some embodiments 1–10 or 2–4 spray nozzles for introduction of organic solvent are employed. In one embodiment said spray nozzle or nozzles for introduction of organic solvent may project into the vessel from the vessel's top. In another embodiment said spray nozzle or nozzles for introduction of organic solvent may be mounted flush with the top of the vessel to help prevent caking of salt. Organic solvent may be sprayed into the vessel as desired and in one embodiment is sprayed into the vessel simultaneously with spraying of solvent media comprising salt through separate spray nozzles.

The rate of introduction of solvent media comprising salt into the vessel containing organic solvent depends upon a number of factors, including, but not limited to, vessel size, temperature of the organic solvent, and the like, and may be determined by one skilled in the art without undue experimentation. In some embodiments, if the rate of introduction is too high, then the temperature of the organic solvent may fall and alkali metal salt may tend to cake. In other embodiments, if the rate of introduction is too low, then process economics are less favorable. In general, the rate of introduction of solvent media comprising salt into the vessel containing organic solvent is as fast as possible to promote rapid devolatilization without excessive caking of the salt. In particular embodiments solvent media comprising salt is introduced into the vessel in such a manner that said media does not impact the walls of the vessel or any stirrer shaft.

The temperature of the organic solvent into which the solvent media comprising salt is sprayed (sometimes referred to hereinafter as devolatilization temperature) is in various embodiments greater than the boiling point of said solvent media under the prevailing pressure; or greater than the boiling point of water under the prevailing pressure; or in a range of between about 75° C. and about 220° C.; or in a range of between about 100° C. and about 200° C.; or in a range of between about 110° C. and about 200° C.; or in a range of between about 130° C. and about 180° C.; or in a range of between about 140° C. and about 160° C. Heat may be provided to the organic solvent using any convenient method. In some embodiments heat is provided to the organic solvent by circulating said solvent through a heat exchanger. In a particular embodiment the heat exchanger is a tube-shell heat exchanger. In another particular embodiment the heat exchanger is a spiral heat exchanger or a self-cleaning reboiler. When the organic solvent comprises the product salt, the rate of flow of the organic solvent-salt mixture through the heat exchanger is such that turbulent flow is achieved to prevent fouling of the heat exchanger by solid salt. Said rate of flow depends upon a number of factors, including, but not limited to, the concentration of salt therein and the temperature, and may be determined without undue experimentation by one skilled in the art.

In one embodiment the vessel holding organic solvent into which the solvent media comprising salt is introduced may be under a positive pressure so that the temperature of organic solvent may be above its normal boiling point at atmospheric pressure. Said vessel may be at a pressure in various embodiments in a range of between about 0 kilopascals (kPa) and about 1400 kPa, or in a range of between about 30 kPa and about 700 kPa, or in a range of between about 30 kPa and about 420 kPa, or in a range of between about 30 kPa and about 350 kPa, or in a range of between about 30 kPa and about 280 kPa, or in a range of between about 65 kPa and about 240 kPa, or in a range of between about 100 kPa and about 210 kPa. In a particular embodiment said vessel may be at a pressure in a range of between about 0 kPa and about 350 kPa. In another embodiment the vessel holding organic solvent into which the solvent media comprising salt is introduced may be under reduced pressure. Operating at reduced pressure tends to lower the distillation temperature of the mixture for devolatilization, and may help limit decomposition of the salt product which may occur at least to some extent at elevated temperatures depending upon the identity of the salt.

During devolatilization of solvent media, any organic solvent exiting the vessel may optionally be replaced by adding additional organic solvent to the vessel. In one embodiment additional organic solvent is added to the vessel simultaneously with devolatilization to keep the total volume of organic solvent substantially the same. As solvent media and organic solvent are removed from the vessel some precipitated salt may be entrained in the distillate. In various embodiments entrained salt may be recovered using any known means. In a particular embodiment entrained salt may be knocked out of the distillate by a spray of organic solvent introduced into a vent through which the distillate with entrained salt passes upon exiting the vessel. The spray of organic solvent may be introduced at an angle to the flow of distillate that is convenient for knocking out at least a portion of entrained salt. In one particular embodiment at least one spray of organic solvent is introduced at an angle to the flow of distillate such that entrained salt is substantially removed, wherein "substantially removed" in the present context means that at least about 80 wt. %, or at least about 85 wt. %, or at least about 90 wt. %, or at least about 95 wt. %, or at least about 97 wt. %, or at least about 98 wt. %, or at least about 99 wt. % of salt is removed, based on the weight of salt originally entrained. Said salt in organic solvent may then be passed back to the vessel.

The salt reaction product may be obtained at a solids level in organic solvent of between about 5% and about 35%, or between about 10% and about 30%, or between about 20% and about 30%. In particular embodiments the salt reaction product may be obtained at a solids level in organic solvent of between about 22% and about 30%, or between about 23% and about 30%, or between about 24% and about 30%.

Before, during or after transfer to another vessel, or before use in any subsequent process such as in a polymerization reaction, the salt product slurry in organic solvent may optionally be subjected to at least one drying step to remove any residual water. Said drying step may include, but is not limited to, combination with additional organic solvent and distillation, optionally at reduced pressure, or distillation of organic solvent from the mixture comprising organic solvent and salt product, optionally with concomitant addition of dry organic solvent at approximately the same rate so as to keep the solvent amount roughly constant. Dry organic solvent in the context of the present process means solvent with less than about 100 ppm water. In one embodiment at least one drying step takes place in the vessel containing organic solvent into which the salt in solvent media was introduced. In other embodiments the salt in organic solvent may be transferred from said vessel to at least one other vessel for a drying step. In particular embodiments the amount of water remaining in the salt-containing organic solvent after one or more drying steps may be less than about 100 ppm, or less than about 60 ppm, or less than about 40 ppm, or less than about 30 ppm, or less than about 20 ppm with respect to the weight of the dry salt present. The amount of water in the salt-containing organic solvent may be determined using known methods. In some embodiments the amount of water in the salt-containing organic solvent may be determined indirectly by measuring the water content of an overhead distillate resulting from distillation of organic solvent. In some embodiments the amount of water in the salt-containing organic solvent before use in a subsequent application, such as a polymerization reaction, is less than about 40 ppm, or less than about 30 ppm, or less than about 20 ppm. The steps of devolatilizing and drying may take place in one vessel, or at least one drying step may take place in a vessel different from the vessel used for the step of devolatilizing.

If desired, the salt product may be separated from the organic solvent using any known method. In particular embodiments separation may be effected by filtration, or centrifugation, or like methods. Remaining traces of organic solvent in the salt may be removed, if desired, by methods such as vacuum drying, air drying or similar operation. It is, however, often convenient to employ the salt in a slurry form in the organic solvent without isolation of the salt. For example, the salt may be employed in slurry form in a subsequent reaction in which said salt is a reactant. In some embodiments the salt in organic solvent may be held in the vessel containing organic solvent into which the salt in solvent media was introduced or in a separate vessel, optionally at a lower temperature (for example, at about 120° C. to about 150° C.), and then transferred to a separate vessel for subsequent reaction.

For some subsequent uses the salt may be advantageously in a certain particle size range. In some embodiments the alkali metal salt has an average particle size below about 100 microns, as determined by laser diffraction using, for example, a Lasentec Size Analyzer. The percentage of particles with diameter greater than about 200 nm is in one embodiment less than about 30%, in another embodiment less than about 25%, and in still another embodiment less than about 20% of the total particles. In other embodiments the percentage of particles with diameter greater than about 500 nm is in one embodiment less than about 5%, in another embodiment less than about 2%, and in still another embodiment less than about 1% of the total particles. In a particular embodiment the percentage of particles with diameter greater than about 200 nm is less than about 25%, and the percentage of particles with diameter greater than about 500 nm is less than about 1%. In one embodiment the desired particle size range may be achieved either before, during or after transfer from the vessel containing organic solvent into which the salt in solvent media was introduced to another vessel, such as a polymerization vessel, or following isolation of salt reaction product, by subjecting salt reaction product to at least one particle size reduction step. In a particular embodiment the salt reaction product may be subjected to at least one particle size reduction step while comprising organic solvent. Said particle size reduction step may employ commercially available equipment, including, but not limited to, one or more centrifugal pumps, grinders, drop-down blenders, particle size reduction homogenizers or delumpers. Particle size reduction equipment may also comprise at least one homogenizer available from Silverson Machines, Inc., East Longmeadow, Mass.

Embodiments of the process for making salt described herein may be performed in batch, continuous or semi-continuous mode. The hydroxy-substituted hydrocarbon salt product may be used in one or more subsequent reactions to form hydroxy-substituted hydrocarbon derivatives. In a particular embodiment a slurry of salt in organic solvent may be used in a reaction to form a monomer for use in condensation polymerization. In another particular embodiment a slurry of hydroxy-substituted hydrocarbon salt in organic solvent may be used directly as a monomer in condensation polymerization. In yet another particular embodiment a slurry of hydroxy-substituted aromatic hydrocarbon salt in organic solvent may be used directly as a monomer in the preparation of polyethers such as, but not limited to, polyetherimides, polyethersulfones, polyetherimidesulfones, polyetherketones, polyetheretherketones, and the like. In an illustrative example the bis(sodium) salt of a dihydroxy-substituted aromatic hydrocarbon may be used as a monomer to form a polyetherimide through reaction with at least one bis(N-(substituted phthalimido))aromatic compound. Suitable substituents on said bis(N-(substituted phthalimido))aromatic compounds include any that can be displaced in a polymerization reaction with the salt of a hydroxy-substituted aromatic hydrocarbon. In particular embodiments suitable substituents include, but are not limited to, nitro, halogen, chloro and bromo. Said polymerization reaction involving the displacement of reactive substituents may be performed in the presence of catalysts known to catalyze said reaction including, but not limited to, at least one hexa-substituted guanidinium salt, such as hexaethylguanidinium chloride. Said polymerization reaction may be performed in at least one solvent of low polarity, usually a solvent substantially lower in polarity than that of the dipolar aprotic solvents previously employed for the preparation of aromatic polyethers. In various embodiments said solvent has a boiling point above about 150° C. in order to facilitate the displacement reaction which typically requires temperatures in the range of between about 125° C. and about 250° C. Suitable solvents of this type include, but are not limited to, ortho-dichlorobenzene, para-dichlorobenzene, dichlorotoluene, 1,2,4-trichlorobenzene, diphenyl sulfone, phenetole, anisole, veratrole and mixtures thereof. Often said polymerization reaction is performed under conditions such that less than about 50 ppm water is present with respect to dry weight of hydroxy-substituted aromatic hydrocarbon salt.

Some embodiments of the invention may be better understood with reference to an illustrative example. In an embodiment of the invention a vessel (sometimes referred to herein as a dryer) is a tank comprising at least one agitator. The agitator design and rate of agitation may be optimized to produce as small a particle size as feasible of the precipitated salt product, and also to facilitate water removal. The agitator design and rate of agitation can be readily determined by one skilled in the art without undue experimentation. The vessel further comprises at least one pressure indicator; at least one temperature indicator; at least one solvent introduction line and at least one solvent return line optionally comprising spray nozzles; inert gas connections; at least one spray nozzle to spray in salt in solvent media; an overheads line leading to at least one and preferably more than one cooled condenser; a back-pressure control valve in the overheads line; an accumulator to receive and decant water, if water is present, from organic solvent; and a pump-around loop for organic solvent, said solvent optionally comprising salt product, leading out of and back into the dryer, said loop comprising a spiral heat exchanger for transferring heat to the organic solvent and a centrifugal pump in the loop. The discharge of organic solvent (optionally containing salt) from the spiral heat exchanger back into the dryer may be through at least one return inlet at the liquid level surface, above the liquid surface level or below the liquid surface level in the dryer. In one particular embodiment the discharge of organic solvent (optionally containing salt) from the spiral heat exchanger back into the dryer is at the liquid level surface in the dryer. The flow rate through the pump-around loop can be optimized to facilitate water removal and heat transfer to organic solvent and in one embodiment is coordinated with the flow rate of solvent media comprising salt into vessel so that the said flow rates are held in a range of specific ratios. A back-pressure is maintained in the pump-around loop to prevent boiling in the heat-exchanger. The pump-around loop comprises at least one back pressure control valve between the exit of the spiral heat exchanger and the return inlet to the dryer. Additional temperature and pressure indicators may be located at appropriate points. Typically the vessel also comprises subsurface baffles to reduce fouling by precipitated salt. Also an optional device or piece of equipment for reducing the particle size of the salt product may be present. If desired, the said particle size reduction device can be placed in the pump-around loop or can simply grind the salt product from the vessel as it is transferred to another vessel, such as to a polymerization reaction vessel. Alternatively, the said particle size reduction device (such as a drop-down blender) can be employed in the vessel itself.

In one particular embodiment salt in solvent media, such as water optionally comprising methanol, is made in a separate tank and then sprayed into the dryer over a time period for devolatilization. The time period will depend upon factors which may include, but are not limited to, the volume of the vessel, the amount of salt to be sprayed and the spray rate. Said time period can readily be determined by one skilled in the art without undue experimentation. In particular embodiments the organic solvent comprises ODCB or toluene, and the devolatilizing step removes both water and organic solvent from the dryer. The organic solvent/solvent media distillate may be condensed and collected in the accumulator. Condensed organic solvent may be pumped back into the dryer, for example after separation from a water layer, to maintain a constant operating level of liquid in the dryer. This organic solvent may also be used to knock down entrained salt in the overhead line, and to spray the sides of the dryer to reduce dryer fouling with precipitated salt product.

Following devolatilization, salt reaction product in the dryer may be optionally subjected to at least one drying step to remove residual water using various methods. In one embodiment extra organic solvent is added in one portion to the dryer after devolatilization is complete. The organic solvent and residual water are then removed by distillation until one obtains salt in organic solvent at a desired solids level and a desired level of dryness. No organic solvent is returned to the dryer during this distillation cycle. In another embodiment, sometimes referred to as the "level control mode", dry organic solvent is fed to the dryer as organic solvent and water are distilled therefrom. The amount of organic solvent supplied to the dryer may be matched to the rate of distillation. In particular embodiments the drying process is run at a temperature of about the boiling point of ortho-dichlorobenzene or toluene. In various embodiments the moisture content of the salt may be inferred by measuring the water content in the organic solvent distilled from the vessel. In some embodiments the level of water in the overhead distillate is less than 20 ppm.

The dryer may be treated to remove extraneous water. In particular embodiments the spray nozzle or nozzles and any valves on the vessel may be plumbed such that organic solvent can be distilled through them to remove moisture that may be retained in these dead spaces. In some embodiments said spray nozzle or nozzles and any valves may comprise a vent through which organic solvent can be distilled. In some embodiments any and all valves and nozzles on the vessel are flush mounted in a position to ensure water cannot linger in dead spaces therein. Dead spaces in the head of the dryer are minimized using techniques known in the art, wherein the head of the dryer is defined as that volume of the dryer above the tangent line from a curved surface at the top of the vessel.

While typical embodiments have been set forth for the purpose of illustration, the foregoing descriptions and examples should not be deemed to be a limitation on the scope of the invention. Accordingly, various modifications, adaptations, and alternatives may occur to one skilled in the art without departing from the spirit and scope of the present invention. It is also anticipated that advances in science and technology will make equivalents and substitutions possible that are not now contemplated by reason of the imprecision of language and these variations should also be construed where possible to be covered by the appended claims. All patents cited herein are incorporated herein by reference.

The invention claimed is:

1. A method for preparing an alkali metal salt of a hydroxy-substituted hydrocarbon which comprises the steps of:
   (i) contacting in a solvent media at least one hydroxy-substituted hydrocarbon with a base comprising an alkali metal cation; and
   (ii) devolatilizing the solvent media comprising alkali metal salt by spraying the solvent media into a substantially water-immiscible organic solvent, said solvent being at a temperature greater than the boiling point of solvent media at the prevailing pressure.

2. The method of claim 1 wherein the hydroxy-substituted hydrocarbon is a hydroxy-substituted aromatic hydrocarbon selected from the group consisting of monohydroxy-substituted aromatic hydrocarbons; dihydroxy-substituted aromatic hydrocarbons; aromatic hydrocarbons substituted with multiple hydroxy groups; trihydroxy-substituted aromatic hydrocarbons; tetrahydroxy-substituted aromatic hydrocarbons; thiohydroxy-substituted aromatic hydrocarbons obtained by replacing one or more hydroxy groups of hydroxy-substituted aromatic hydrocarbons with thiohydroxy groups and mixtures of these substituted aromatic hydrocarbons.

3. The method of claim 2 wherein the hydroxy-substituted aromatic hydrocarbon is at least one monohydroxy-substituted aromatic hydrocarbon selected from the group consisting of phenol, alkyl phenols, o-cresol, m-cresol, p-cresol, p-cumylphenol, resorcinol monomethyl ether, 1-naphthol, 2-naphthol, p-chlorophenol, o-chlorophenol and mixtures thereof.

4. The method of claim 2 wherein the hydroxy-substituted aromatic hydrocarbon is at least one dihydroxy-substituted aromatic hydrocarbon of the formula (I):

wherein D has the structure of formula (II):

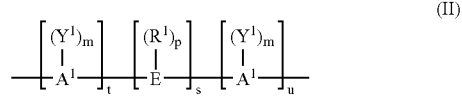

wherein $A_1$ represents an aromatic group;

E comprises a sulfur-containing linkage, sulfide, sulfoxide, sulfone; a phosphorus-containing linkage, phosphinyl, phosphonyl; an ether linkage; a carbonyl group; a tertiary nitrogen group; a silicon-containing linkage; silane; a cycloaliphatic group; cyclopentylidene, 3,3,5-trimethylcyclopentylidene, cyclohexylidene, 3,3-dimethycyclohexylidene, 3,3,5-trimethylcyclohexylidene, methylcyclohexylidene, 2-[2.2.1]-bicycloheptylidene, neopentylidene, cyclopentadecylidene, cyclododecylidene, adamantylidene; an alkylene or alkylidene group, which group; which group may optionally by part of one or more fused rings attached to one or more aromatic groups bearing one hydroxy substituent; an unsaturated alkylidene group; or two or more alkylene or alkylidene groups connected by a moiety different from alkylene or alkylidene and selected from the group consisting of an aromatic linkage, a tertiary nitrogen linkage; an ether linkage; a carbonyl linkage; a silicon-containing linkage, silane, siloxy; a sulphur-containing linkage, sulfide, sulfoxide, sulfone; a phosphorus-containing linkage, phosphinyl, and phosphonyl;

$R^1$ comprises hydrogen; a monovalent hydrocarbon group, alkenyl, allyl, alkyl, aryl, aralkyl, alkaryl, or cycloalkyl;

$Y^1$ independently at each occurrence is selected from the group consisting of an inorganic atom, a halogen; an inorganic group, a nitro group; an organic group, a monovalent hydrocarbon group, alkenyl, allyl, alkyl, aryl, aralkyl, alkaryl, cycloalkyl and a alkoxy group;

the letter "m" represents any integer from and including zero through the number of positions on $A^1$ available for substitution;

the letter "p" represents an integer from and including zero through the number of positions on E available for substitution;

the letter "t" represents an integer equal to at least one;

the letter "s" represents an integer equal to either zero or one; and the letter "u" represents any integer including zero.

5. The method of claim 2 wherein the hydroxy-substituted aromatic hydrocarbon is at least one dihydroxy-substituted aromatic hydrocarbon selected from the group consisting of 4,4'-(cyclopentylidene)diphenol; 4,4'-(3,3,5-trimethylcyclopentylidene)diphenol; 4,4'-(cyclohexylidene)diphenol; 4,4'-(3,3-dimethylcyclohexylidene)diphenol; 4,4'-(3,3,5-trimethylcyclohexylidene)diphenol; 4,4'-(methylcyclohexylidene) diphenol; 4,4'-bis(3,5-dimethyl)diphenol, 1,1-bis(4-hydroxy-3-methylphenyl)cyclohexane; 4,4-bis(4-hydroxyphenyl)heptane; 2,4'-dihydroxydiphenylmethane; bis(2-hydroxyphenyl)methane; bis(4-hydroxyphenyl)methane; bis(4-hydroxy-5-nitrophenyl)methane; bis(4-hydroxy-2,6-dimethyl-3-methoxyphenyl)methane; 1,1-bis(4-hydroxyphenyl)ethane; 1,2-bis(4-hydroxyphenyl)ethane; 1,1-bis(4-hydroxy-2-chlorophenyl)ethane; 2,2-bis(4-hydroxyphenyl) propane; 2,2-bis(3-phenyl-4-hydroxyphenyl)propane; 2,2-bis(4-hydroxy-3-methylphenyl)propane; 2,2-bis(4-hydroxy-3-ethylphenyl)propane; 2,2-bis(4-hydroxy-3-isopropylphenyl)propane; 2,2-bis(4-hydroxy-3,5-dimethylphenyl)propane; 3,5,3',5'-tetrachloro-4,4'-dihydroxyphenylpropane; bis(4-hydroxyphenyl) cyclohexylmethane; 2,2-bis(4-hydroxyphenyl)-1-phenylpropane; 2,4'-dihydroxyphenyl sulfone; dihydroxy naphthalene, 2,6-dihydroxy naphthalene; catechol; hydroquinone; resorcinol; $C_{1-3}$ alkyl-substituted resorcinols; 2,2-bis(4-hydroxyphenyl)butane; 2,2-bis(4-hydroxyphenyl)-2-methylbutane; 1,1-bis(4-hydroxyphenyl)cyclohexane; biphenol; bis(4-hydroxyphenyl); bis(4-hydroxyphenyl) ether; bis(4-hydroxyphenyl)sulfide; 2-(3-methyl-4-hydroxyphenyl-2-(4-hydroxyphenyl)propane; 2-(3,5-dimethyl-4-hydroxyphenyl)-2-(4-hydroxyphenyl)propane; 2-(3-methyl-4-hydroxyphenyl)-2-(3,5-dimethyl-4-hydroxyphenyl) propane; bis(3,5-dimethylphenyl-4-hydroxyphenyl) methane; 1,1-bis(3,5-dimethylphenyl-4-hydroxyphenyl) ethane; 2,2-bis(3,5-dimethylphenyl-4-hydroxyphenyl) propane; 2,4-bis(3,5-dimethylphenyl-4-hydroxyphenyl)-2-methylbutane; 3,3-bis(3,5-dimethylphenyl-4-hydroxyphenyl)pentane; 1,1-bis(3,5-dimethylphenyl-4- hydroxyphenyl)cyclopentane; 1,1-bis(3,5-dimethylphenyl-4bis(3,5-dimethylphenyl-4-hydroxyphenyl)sulfide, 3-(4-hydroxyphenyl)-1,1,3-trimethylindan-5-ol, 1-(4-hydroxyphenyl)-1,3,3-trimethylindan-5-ol, 2,2,2',2'-tetrahydro-3,3,3',3'-tetramethyl-1,1'-spirobi [1H-indene]-6,6'-diol, and mixtures thereof, or wherein the hydroxy-substituted aromatic hydrocarbon is tris(4-hydroxyphenyl) ethane.

6. The method of claim 2 wherein the hydroxy-substituted aromatic hydrocarbon is at least one dihydroxy-substituted aromatic hydrocarbon selected from the group consisting of those of the formula (III):

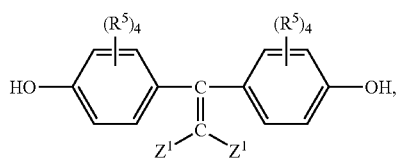

where independently each $R^5$ is hydrogen, chlorine, bromine or a $C_{1-30}$ monovalent hydrocarbon or hydrocarbonoxy group, each $Z^1$ is hydrogen, chlorine or bromine, subject to the provision that at least one $Z^1$ is chlorine or bromine; and those of the formula (IV):

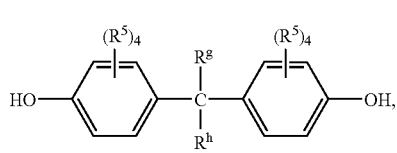

where independently each $R^5$ is as defined hereinbefore, and $R^g$ and $R^h$ are each independently hydrogen or a $C_{1-30}$ hydrocarbon group.

7. The method of claim 2 wherein the hydroxy-substituted aromatic hydrocarbon comprises bisphenol A.

8. The method of claim 1 wherein the solvent media comprises water.

9. The method of claim 8 wherein the amount of water removed during devolatilizing is greater than about 95 wt. %.

10. The method of claim 8 wherein the amount of water removed during devolatilizing is greater than about 98 wt. %.

11. The method of claim 8 wherein the amount of water removed during devolatilizing is greater than about 99 wt. %.

12. The method of claim 8 wherein the solvent media further comprises at least one water-soluble protic organic solvent.

13. The method of claim 12 wherein the water-soluble protic organic solvent comprises methanol or butanol.

14. The method of claim 1 wherein the solvent media comprises at least one water-soluble protic organic solvent.

15. The method of claim 1 wherein the alkali metal salt is essentially soluble in the solvent media.

16. The method of claim 1 wherein the alkali metal cation is sodium.

17. The method of claim 1 wherein the base is sodium hydroxide or sodium methoxide.

18. The method of claim 1 wherein the amounts of hydroxy-substituted hydrocarbon and base in step (i) are stoichiometric, or deviate from stoichiometry by an amount in a range of between about 0.01 and about 1.2 mole %.

19. The method of claim 1 wherein the amounts of hydroxy-substituted hydrocarbon and base in step (i) deviate from stoichiometry by no more than plus/minus 0.4 mole %.

20. The method of claim 1 wherein the organic solvent is at least one member selected from the group consisting of alkylated benzenes, toluene, xylene, phenetole, anisole, veratrole, diphenylsulfone, halogenated benzenes, chlorinated benzenes, chlorobenzene, dichlorotoluene, dichlorobenzene, ortho-dichlorobenzene, para-dichlorobenzene, and 1,2,4-trichlorobenzene.

21. The method of claim 1 wherein the organic solvent is toluene or ortho-dichlorobenzene.

22. The method of claim 1 wherein the organic solvent is at a temperature in a range of between about 75° C. and about 220° C.

23. The method of claim 1 wherein the organic solvent is at a temperature in a range of between about 100° C. and about 220° C.

24. The method of claim 1 wherein the organic solvent is at a temperature in a range of between about 110° C. and about 200° C.

25. The method of claim 1 wherein the organic solvent is at a temperature in a range of between about 130° C. and about 180° C.

26. The method of claim 1 wherein the organic solvent is at a temperature in a range of between about 140° C. and about 160° C.

27. The method of claim 1 wherein the alkali metal salt is substantially insoluble in the organic solvent at the devolatilization temperature.

28. The method of claim 1 wherein heat is provided to the organic solvent by circulating said solvent, optionally comprising alkali metal salt, through a pump-around loop comprising a centrifugal pump, and a spiral heat exchanger or a self-cleaning reboiler.

29. The method of claim 1 wherein devolatilizing is performed in a vessel comprising subsurface baffles, at least one agitator and at least one spray nozzle for introduction of solvent media comprising alkali metal salt.

30. The method of claim 29 wherein there is at least one gap between any baffle and the side of the vessel.

31. The method of claim 1 further comprising at least one drying step after the devolatilizing step.

32. The method of claim 31 wherein the drying step comprises distilling organic solvent and water from the vessel either with or without introduction of dry organic solvent to the vessel.

33. The method of claim 31 wherein the amount of water remaining in the salt-containing organic solvent after one or more drying steps is less than about 100 ppm.

34. The method of claim 31 wherein the amount of water remaining in the salt-containing organic solvent after one or more drying steps is less than about 20 ppm.

35. The method of claim 31 wherein steps of devolatilizing and drying take place in one vessel.

36. The method of claim 31 wherein the drying step takes place in a vessel different from the vessel used for the step of devolatilizing.

37. The method of claim 1 wherein the alkali metal salt comprises less than 25% of particles with a diameter of greater than about 200 nm.

38. The method of claim 1 wherein the alkali metal salt comprises less than 5% of particles with a diameter of greater than about 500 nm.

39. The method of claim 1 wherein the alkali metal salt comprises less than 2% of particles with a diameter of greater than about 500 nm.

40. The method of claim 1 further comprising at least one step of reducing the alkali metal salt particle size.

41. The method of claim 40 wherein the particle size is reduced using equipment which comprises one or more of a centrifugal pump, grinder, drop-down blender, particle size reduction homogenizer or delumper.

42. The method of claim 40 wherein the particle size reduction step is performed on a slurry of the alkali metal salt in organic solvent.

43. The method of claim 1 wherein the alkali metal salt in organic solvent is at a solids level in a range of between about 5% and about 32% following devolatilizing.

44. The method of claim 1 wherein the alkali metal salt in organic solvent is at a solids level in a range of between about 10% and about 20% following devolatilizing.

45. A method for preparing a disodium salt of a dihydroxy-substituted aromatic hydrocarbon which comprises the steps of:
(i) contacting at least one dihydroxy-substituted aromatic hydrocarbon with sodium hydroxide in solvent media comprising water, wherein the amounts of dihydroxy-substituted aromatic hydrocarbon and sodium hydroxide deviate from stoichiometry by no more than plus/minus 0.4 mole %, and wherein the alkali metal salt is essentially soluble in the solvent media;
(ii) devolatilizing the solvent media comprising the disodium salt by spraying the solvent media into a substantially water-immiscible organic solvent in a vessel comprising subsurface baffles, at least one agitator and at least one spray nozzle for introduction of solvent media, wherein said organic solvent is at a temperature in a range of between about 110° C. and about 200° C., wherein heat is provided to the organic solvent by circulating said solvent, optionally comprising disodium salt, through a pump-around loop comprising a centrifugal pump, and a spiral heat exchanger or a self-cleaning reboiler; wherein the amount of water removed during devolatilizing is greater than about 99 wt. %; and wherein said salt is at a solids level in a range of between about 10% and about 20% following devolatilizing; and
(iii) reducing the disodium salt particle size at least once in a slurry of the organic solvent.

46. The method of claim 45 wherein the hydroxy-substituted aromatic hydrocarbon is bisphenol A.

47. The method of claim 45 wherein the organic solvent is toluene or ortho-dichlorobenzene.

48. The method of claim 47 wherein the organic solvent is ortho-dichlorobenzene.

49. The method of claim 48 wherein the ortho-dichlorobenzene is at a temperature in a range of between about 130° C. and about 180° C.

50. The method of claim 45 wherein the particle size is reduced using equipment which comprises one or more of a centrifugal pump, grinder, drop-down blender, particle size reduction homogenizer or delumper.

51. The method of claim 45 further comprising at least one drying step to remove residual water remaining after the devolatilizing step, wherein said drying step comprises distilling organic solvent and water from the vessel either with or without introduction of dry organic solvent to the vessel.

52. The method of claim 51 wherein the amount of water remaining in the salt-containing organic solvent after one or more drying steps is less than about 20 ppm.

53. The method of claim 51 wherein steps of devolatilizing and drying take place in one vessel.

54. The method of claim 45 wherein the disodium salt comprises less than 25% of particles with a diameter of greater than about 200 nm; and less than 2% of particles with a diameter of greater than about 500 nm.

55. A method for preparing the disodium salt of bisphenol A which comprises the steps of:
(i) contacting bisphenol A with sodium hydroxide in solvent media comprising water, wherein the amounts of bisphenol A and sodium hydroxide deviate from stoichiometry by no more than plus/minus 0.4 mole %;
(ii) devolatilizing the solvent media comprising the disodium salt by spraying the solvent media into ortho-dichlorobenzene in a vessel comprising subsurface baffles, at least one agitator and at least one spray nozzle for introduction of solvent media, wherein said ortho-dichlorobenzene is at a temperature in a range of between about 130° C. and about 180° C., wherein heat is provided to the ortho-dichlorobenzene by circulating said ortho-dichlorobenzene, optionally comprising disodium salt, through a pump-around loop comprising a centrifugal pump, and a spiral heat exchanger or a self-cleaning reboiler; wherein the amount of water removed during devolatilizing is greater than about 99 wt. %; and wherein said salt is at a solids level in a range of between about 10% and about 20% following devolatilizing;
(iii) reducing the disodium salt particle size at least once in a slurry of ortho-dichlorobenzene to provide said disodium salt comprising less than 25% of particles with a diameter of greater than about 200 nm; and less than 2% of particles with a diameter of greater than about 500 nm, wherein the particle size is reduced using equipment which comprises one or more of a centrifugal pump, grinder, drop-down blender, particle size reduction homogenizer or delumper; and
(iv) drying at least once to remove residual water remaining after step (iii), wherein said drying step comprises distilling ortho-dichlorobenzene and water from the vessel either with or without introduction of dry ortho-dichlorobenzene to the vessel to provide said disodium salt with an amount of water remaining after one or more drying steps of less than about 20 ppm.

56. A method for preparing an alkali metal salt of a hydroxy-substituted aromatic hydrocarbon which comprises the steps of:
(i) contacting at least one hydroxy-substituted aromatic hydrocarbon with a base in solvent media comprising water and at least one water-soluble protic organic solvent, wherein the amounts of hydroxy-substituted aromatic hydrocarbon and base deviate from stoichiometry by no more than plus/minus 0.4 mole %, and wherein the alkali metal salt is essentially soluble in the solvent media;
(ii) devolatilizing the solvent media comprising the salt by adding the solvent media into a substantially water-immiscible organic solvent in a vessel comprising subsurface baffles, at least one agitator and at least one inlet for introduction of solvent media, wherein said organic solvent is at a temperature in a range of between about 110° C. and about 200° C., wherein heat is provided to the organic solvent by circulating said solvent, optionally comprising disodium salt, through a pump-around loop comprising a centrifugal pump, and a spiral heat exchanger or a self-cleaning reboiler; wherein the amount of water removed during devolatilizing is greater than about 99 wt. %; and wherein said salt is at a solids level in a range of between about 10% and about 20% following devolatilizing; and (iii) reducing the salt particle size at least once in a slurry of the organic solvent.

57. The method of claim 56 wherein the hydroxy-substituted aromatic hydrocarbon is a dihydroxy-substituted aromatic hydrocarbon.

58. The method of claim 57 wherein the dihydroxy-substituted aromatic hydrocarbon is bisphenol A.

59. The method of claim 56 wherein the alkali metal cation is sodium.

60. The method of claim 56 wherein the base is sodium hydroxide.

61. The method of claim 56 wherein the water-soluble protic organic solvent comprises methanol.

62. The method of claim 56 wherein the organic solvent is toluene or ortho-dichlorobenzene.

63. The method of claim 62 wherein the organic solvent is ortho-dichlorobenzene.

64. The method of claim 63 wherein the ortho-dichlorobenzene is at a temperature in a range of between about 130° C. and about 180° C.

65. The method of claim 56 wherein the particle size is reduced using equipment which comprises one or more of a centrifugal pump, grinder, drop-down blender, particle size reduction homogenizer or delumper.

66. The method of claim 56 further comprising at least one drying step to remove residual water remaining after the devolatilizing step, wherein said drying step comprises distilling a mixture comprising organic solvent and water from the vessel either with or without introduction of dry organic solvent to the vessel.

67. The method of claim 66 wherein the amount of water remaining in the salt-containing organic solvent after one or more drying steps is less than about 20 ppm.

68. The method of claim 67 wherein steps of devolatilizing and drying take place in one vessel.

69. The method of claim 56 wherein the salt comprises less than 25% of particles with a diameter of greater than about 200 nm; and less than 2% of particles with a diameter of greater than about 500 nm.

70. A method for preparing the disodium salt of bisphenol A which comprises the steps of:

(i) contacting bisphenol A with sodium hydroxide in solvent media comprising water and methanol, wherein the amounts of bisphenol A and sodium hydroxide deviate from stoichiometry by no more than plus/minus 0.4 mole %;

(ii) devolatilizing the solvent media comprising the disodium salt by adding the solvent media to ortho-dichlorobenzene in a vessel comprising subsurface baffles, at least one agitator and at least one inlet for introduction of solvent media, wherein said ortho-dichlorobenzene is at a temperature in a range of between about 130° C. and about 180° C., wherein heat is provided to the ortho-dichlorobenzene by circulating said ortho-dichlorobenzene, optionally comprising disodium salt, through a pump-around loop comprising a centrifugal pump, and a spiral heat exchanger or a self-cleaning reboiler; wherein the amount of water removed during devolatilizing is greater than about 99 wt. %; and wherein said salt is at a solids level in a range of between about 10% and about 20% following devolatilizing;

(iii) reducing the disodium salt particle size at least once in a slurry of ortho-dichlorobenzene to provide said disodium salt comprising less than 25% of particles with a diameter of greater than about 200 nm; and less than 2% of particles with a diameter of greater than about 500 nm, wherein the particle size is reduced using equipment which comprises one or more of a centrifugal pump, grinder, drop-down blender, particle size reduction homogenizer or delumper; and (iv) drying at least once to remove residual water remaining after step (iii), wherein said drying step comprises distilling ortho-dichlorobenzene and water from the vessel either with or without introduction of dry ortho-dichlorobenzene to the vessel to provide said disodium salt with an amount of water remaining after one or more drying steps of less than about 20 ppm.

* * * * *